(12) United States Patent
Oh et al.

(10) Patent No.: US 10,661,079 B2
(45) Date of Patent: May 26, 2020

(54) APPARATUS FOR INSERTION OF NERVE ELECTRODES

(71) Applicant: KOREA INSTITUTE OF SCIENCE AND TECHNOLOGY, Seoul (KR)

(72) Inventors: Sang Rok Oh, Gangneung-si (KR); Keehoon Kim, Seoul (KR); Sehyuk Yim, Seoul (KR); Jinwoo Jeong, Gangneung-si (KR); Yong Seok Ihn, Seoul (KR); Donghyun Hwang, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 166 days.

(21) Appl. No.: 15/907,832

(22) Filed: Feb. 28, 2018

(65) Prior Publication Data

US 2019/0060638 A1 Feb. 28, 2019

(30) Foreign Application Priority Data

Aug. 28, 2017 (KR) .......................... 10-2017-0108811

(51) Int. Cl.
*A61N 1/05* (2006.01)
*A61B 17/34* (2006.01)

(52) U.S. Cl.
CPC ........ *A61N 1/0551* (2013.01); *A61B 17/3468* (2013.01); *A61N 1/0558* (2013.01); *A61N 1/0529* (2013.01)

(58) Field of Classification Search
CPC .. A61N 1/0504; A61N 1/0558; A61N 1/0556; A61N 1/0551; A61N 1/3605; A61N 1/05; A61B 17/3468; A61B 1/0529; A61B 5/6877; A61B 5/6868; A61C 5/46

USPC .......................... 606/129; 607/115, 116, 118
See application file for complete search history.

(56) References Cited

U.S. PATENT DOCUMENTS

| | | | |
|---|---|---|---|
| 5,361,760 A | 11/1994 | Normann et al. | |
| 6,304,785 B1 * | 10/2001 | McCreery | A61N 1/0541 128/899 |
| 7,797,058 B2 * | 9/2010 | Mrva | A61N 1/0556 606/129 |
| 8,226,661 B2 | 7/2012 | Balling et al. | |
| 8,774,944 B2 | 7/2014 | Thenuwara et al. | |
| 2010/0145221 A1 * | 6/2010 | Brunnett | A61B 5/0488 600/554 |

(Continued)

OTHER PUBLICATIONS

Sehyuk Yim et al., "A Handheld Device for Magnetically Inserting a Neural Interface into a Peripheral Nervous System", Annual International Conference of the IEEE Engineering in Medicine and Biology Society, 2017, pp. 226-229.

(Continued)

*Primary Examiner* — Gregory A Anderson
*Assistant Examiner* — Alyssa M Keane
(74) *Attorney, Agent, or Firm* — Rabin & Berdo, P.C.

(57) ABSTRACT

An apparatus for inserting an electrode structure into nerve in tissue of a living body includes a nerve fixing part which fixes the nerve such that at least part of the nerve is hung thereon, and an electrode structure ejector on which the electrode structure is mounted, and which moves the electrode structure in insertion direction to insert the electrode structure into the fixed part of the nerve, wherein the nerve fixing part and the electrode structure ejector are disposed on the same axis.

14 Claims, 11 Drawing Sheets

(56) References Cited

U.S. PATENT DOCUMENTS

2018/0221653 A1* 8/2018 Kim .................... A61N 1/0556

OTHER PUBLICATIONS

J. U Chu, "Recording and Analysis of Peripheral Nerve Activity Using Multi-Electrode Array", Journal of Rehabilitation Welfare Engineering & Assistive Technology, 2016, pp. 279-285, vol. 10, No. 4.

* cited by examiner

APPARATUS FOR INSERTION OF NERVE ELECTRODES

DESCRIPTION OF GOVERNMENT-SPONSORED RESEARCH AND DEVELOPMENT

This research is sponsored by National Research Foundation of Korea, Ministry of Science and ICT under the supervision of Korea Institute of Science and Technology (Development of bio-signal measurement and analysis system for movement and tactile transmission and a bionic arm with bio-signal based control function, Project No. 1711042768).

CROSS-REFERENCE TO RELATED APPLICATION

This application claims priority to Korean Patent Application No. 10-2017-0108811, filed on Aug. 28, 2017, and all the benefits accruing therefrom under 35 U.S.C. § 119, the contents of which in its entirety are herein incorporated by reference.

BACKGROUND

1. Field

The present disclosure relates to an apparatus for inserting an electrode structure, and more particularly, to an apparatus for inserting an electrode structure to fix the electrode structure into nerve in tissue of a living body.

2. Description of the Related Art

Studies have been intensively made to define how the nerve works by stimulating the nerve or obtaining and analyzing neural signals. For these studies, a task for inserting an invasive electrode structure into a desired location of the nerve should be performed first.

Because nerves such as peripheral nerves are generally surrounded by the tough and strong outermost covering, an assistive tool is needed to insert the invasive electrode structure into the nerve. Conventional apparatus for inserting an electrode structure allows a user to eject the electrode structure using air pressure and fix it to the nerve.

In case of the conventional pneumatic apparatus for inserting an electrode structure, insertion is accompanied by strong impacts, which may damage the nerve or the electrode structure. According to the conventional method, it requires to predict a point of aim in order to control the direction of the apparatus, which makes it difficult to precisely insert the electrode structure into a desired location of the nerve, and an extra device may be necessary to increase precision. Additionally, to enable precise insertion, the conventional apparatus for inserting an electrode structure needs to be fixed for use, resulting in low convenience in use.

RELATED LITERATURES

Patent Literatures (Patent Literature 1) U.S. Pat. No. 5,361,760 (1994, Nov. 8)

SUMMARY

The present disclosure is designed to solve the above-mentioned conventional problem, and therefore, the present disclosure is directed to providing an apparatus for inserting an electrode structure, including a device for fixing nerve and an electrode structure ejection device on the same axis to insert the electrode structure into the nerve precisely with a small force.

To achieve the above object, according to an aspect of the present disclosure, there is provided an apparatus for inserting an electrode structure into nerve in tissue of a living body, including a nerve fixing part which fixes the nerve such that at least part of the nerve is hung thereon, and an electrode structure ejector on which the electrode structure is mounted and which moves the electrode structure in insertion direction to insert the electrode structure into the fixed part of the nerve, wherein the nerve fixing part and the electrode structure ejector are disposed on the same axis.

According to an embodiment of the present disclosure, the nerve fixing part may include an alignment slit disposed on the same axis as the electrode structure ejector to assist a linear movement of the electrode structure, and the electrode structure may move along the alignment slit and may be inserted into the nerve.

According to an embodiment of the present disclosure, the apparatus for inserting an electrode structure may further include a pull lever which moves the nerve fixing part to further fix the nerve to a front end of the apparatus for inserting an electrode structure.

According to an embodiment of the present disclosure, the apparatus for inserting an electrode structure may further include a pressing part which applies a force to the electrode structure ejector to move the electrode structure in the insertion direction.

According to an embodiment of the present disclosure, the apparatus for inserting an electrode structure may further include a first elastic element disposed on top of the nerve fixing part to fix the nerve fixing part, wherein the first elastic element is compressed when a force equal to or greater than a first critical value is applied, and a second elastic element disposed on bottom of the electrode structure ejector to fix the electrode structure ejector, wherein the second elastic element is compressed when a force equal to or greater than a second critical value is applied.

According to an embodiment of the present disclosure, the second critical value may be greater than the first critical value.

According to an embodiment of the present disclosure, at least part of the nerve fixing part that touches the nerve may be made of elastomer.

According to an embodiment of the present disclosure, the nerve fixing part may include a fixing groove which fixes the nerve such that the nerve is hung thereon, and the fixing groove may have a width that is controllable to fit a diameter of the nerve.

According to an embodiment of the present disclosure, the electrode structure may include at least one probe which penetrates the nerve and has an electrode.

According to an embodiment of the present disclosure, the electrode structure may be mounted in a mounting part of a size that matches a width of the electrode structure, and as the electrode structure ejector moves in the insertion direction, a force may be applied to a rear end the electrode structure and thereby the electrode structure may be ejected through an opening connected to the mounting part.

The apparatus according to various embodiments of the present disclosure may stably and effectively insert an invasive electrode structure into nerve. Additionally, the apparatus proposed by the present disclosure can be easily manipulated with a user's hand, providing the improved convenience in use, and may accurately insert the electrode structure into a desired location of the nerve with little or no damage.

The effects that can be obtained from the present disclosure are not limited to the above-mentioned effects, and other effects not mentioned herein will be clearly understood by those skilled in the art from the following disclosure.

DETAILED DESCRIPTION

Hereinafter, exemplary embodiments of the present disclosure will be described with reference to the accompanying drawings. The present disclosure is described with reference to the embodiments shown in the drawings, but this is described for illustration only, and the technical spirit of the present disclosure and its key elements and operation are not limited thereby.

Figure 1:
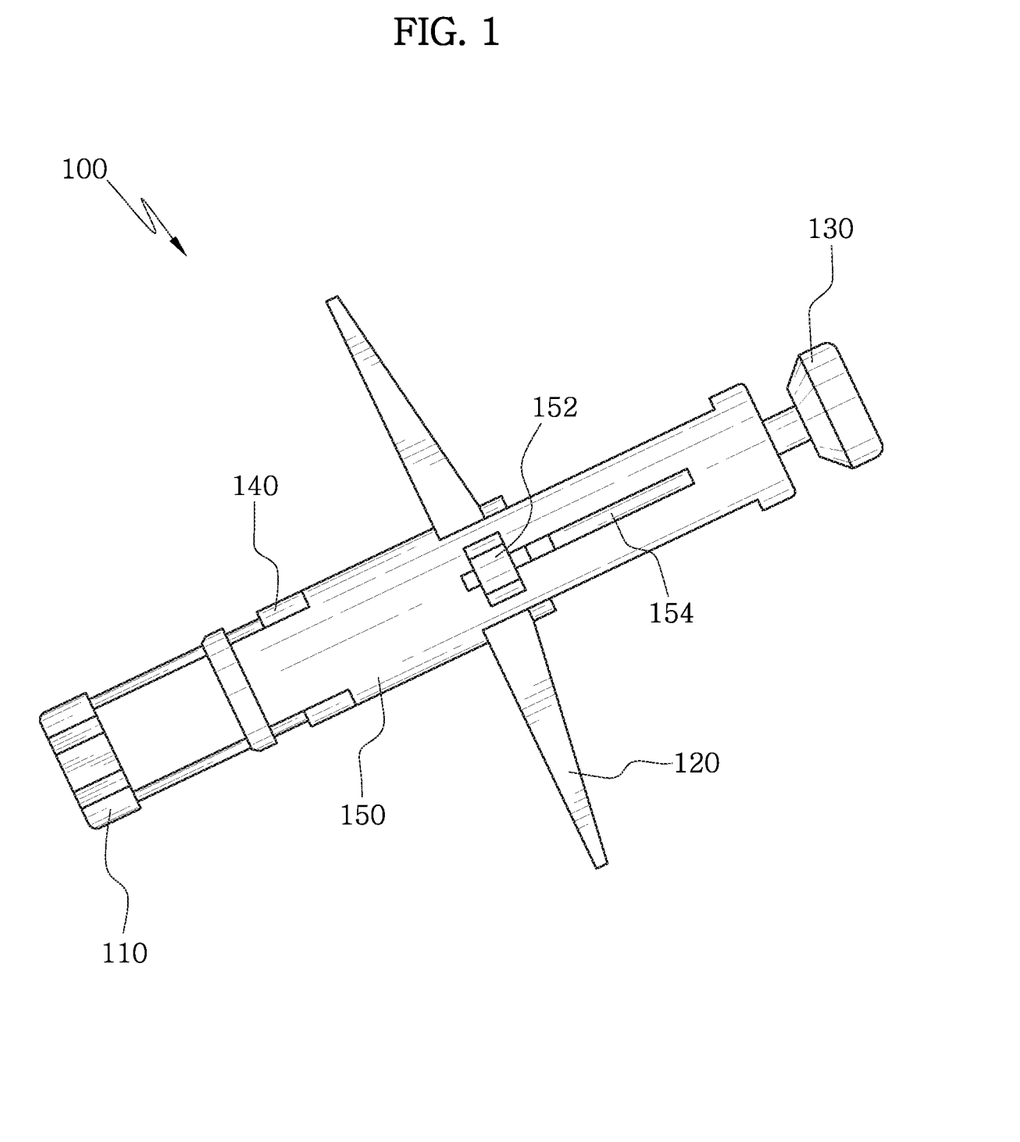
FIG. 1 is a perspective view of an apparatus for inserting an electrode structure according to an embodiment of the present disclosure.
Figure 2:
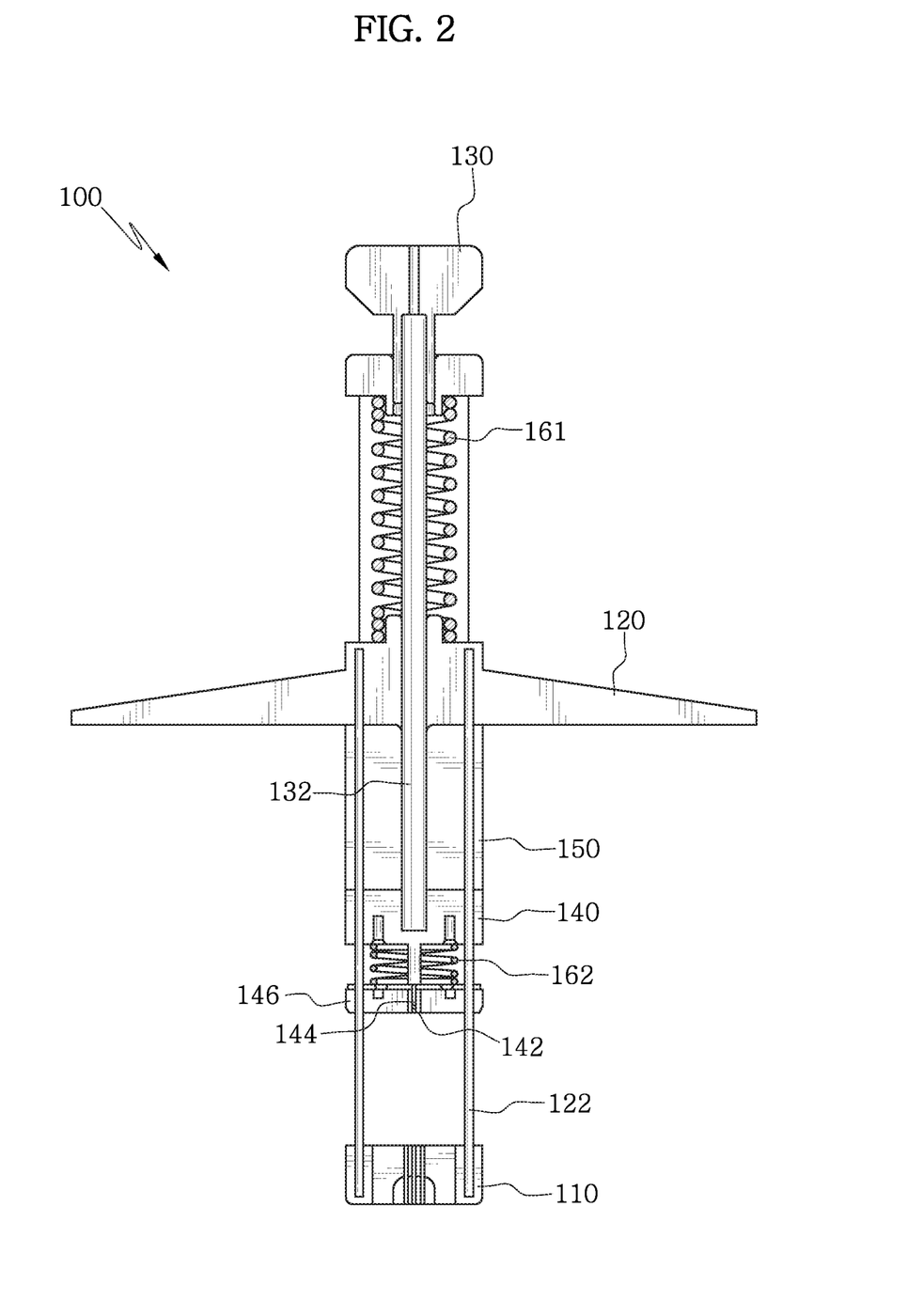
FIG. 2 is a longitudinal cross-sectional view of the apparatus for inserting an electrode structure of FIG. 1.

FIGS. 1 and 2 are a perspective view and a longitudinal cross-sectional view of an apparatus 100 for inserting an electrode structure according to an embodiment of the present disclosure, respectively.

Referring to FIGS. 1 and 2, the apparatus 100 for inserting an electrode structure according to an embodiment of the present disclosure includes a nerve fixing part 110, a pull lever 120, a pressing part 130, an electrode structure ejector 140, a body 150, a movement element 152 and a movement groove 154.

The nerve fixing part 110 is formed with a structure that fixes the nerve to enable accurate targeting at a desired location of the nerve. According to an embodiment of the present disclosure, the nerve fixing part 110 may include a groove structure on which the nerve can be hung.

The pull lever 120 is connected to a sliding element 122, and the end of the sliding element 122 is connected to the nerve fixing part 110. When a force greater than a threshold is applied to the pull lever 120, the pull lever 120 moves in the pull direction along a center pole 132. As the pull lever 120 moves, the sliding element 122 and the nerve fixing part 110 connected thereto also move in the pull direction.

Through this movement, a nerve fixing plate 146 comes into contact with one side of the nerve, and a target site of the nerve placed on the nerve fixing part 110 may be stably fixed. When the pull lever 120 is manipulated to move the apparatus 100 for inserting an electrode structure in a direction opposite to the movement of the nerve fixing part 110, sagging of the nerve may be prevented.

The pressing part 130 is connected to the center pole 132 to move the electrode structure ejector 140. According to an embodiment of the present disclosure, when a force equal to or greater than a critical value is applied to the pressing part 130, the pressing part 130 moves the electrode structure ejector 140 and thereby ejects an electrode structure 144 through an opening 142.

The electrode structure ejector 140 is connected to the pressing part 130 through the center pole 132. The electrode structure ejector 140 moves toward the nerve by the force applied to the pressing part 130, and through this, the electrode structure 144 may be inserted into the target site of the nerve fixed by the nerve fixing part 110. To allow the electrode structure 144 to be accurately inserted into the target site of the nerve only by the linear movement of the electrode structure ejector 140, the electrode structure ejector 140 and the nerve fixing part 110 may be placed on the same axis. The electrode structure 144 is manufactured with nearly the same width as the opening 142 so that the electrode structure 144 may be loaded in a mounting part connected to the opening 142.

The body 150 includes the center pole 132 therein, and has the pull lever 120 and the electrode structure ejector 140. The body 150 may include a shape that is open along the path on which the pull lever 120 moves. According to an embodiment of the present disclosure, the body 150 may further include the movement element 152 and the movement groove 154. The movement element 152 is connected to the pull lever 120, and moves as much as the same distance along the movement groove 154 while the pull lever 120 moves. The compression length of a first elastic element 161 and the movement distance of the nerve fixing part 110 may be inferred through a relative location of the movement element 152 to the movement groove 154. According to another embodiment of the present disclosure, the movement element 152 and the movement groove 154 may be omitted.

As shown in FIG. 2, the apparatus 100 for inserting an electrode structure may further include a first elastic element 161 and/or a second elastic element 162.

The first elastic element 161 is disposed between the pull lever 120 and the end of the body 150 to place the pull lever 120 in fixed state. The first elastic element 161 is configured to be compressed when a force equal to or greater than a first critical value is applied to the pull lever 120, so that the nerve fixing part 110 moves in the pull direction.

The second elastic element 162 is disposed between the electrode structure ejector 140 and the nerve fixing plate 146 to place the electrode structure ejector 140 in fixed state. The second elastic element 162 is formed to be compressed when a force equal to or greater than a second critical value is applied to the pressing part 130, and through this, the electrode structure 144 is ejected through the opening 142.

According to an embodiment of the present disclosure, each of the first elastic element 161 and the second elastic element 162 may be a spring, and the stiffness of the second elastic element 162 may be greater than the stiffness of the first elastic element 161. In other words, the first elastic element 161 and the second elastic element 162 may be properly selected such that the second critical value, or the magnitude of a force when the second elastic element 162 starts to be compressed, is greater than the first critical value, or the magnitude of a force when the first elastic element 161 starts to be compressed. In this case, insertion of the electrode structure is accomplished through sequential steps, and stable insertion of the electrode structure is achieved. However, the present disclosure is not limited to the above-mentioned embodiment, and any known elastic body may be used for the elastic element.

Figure 3:
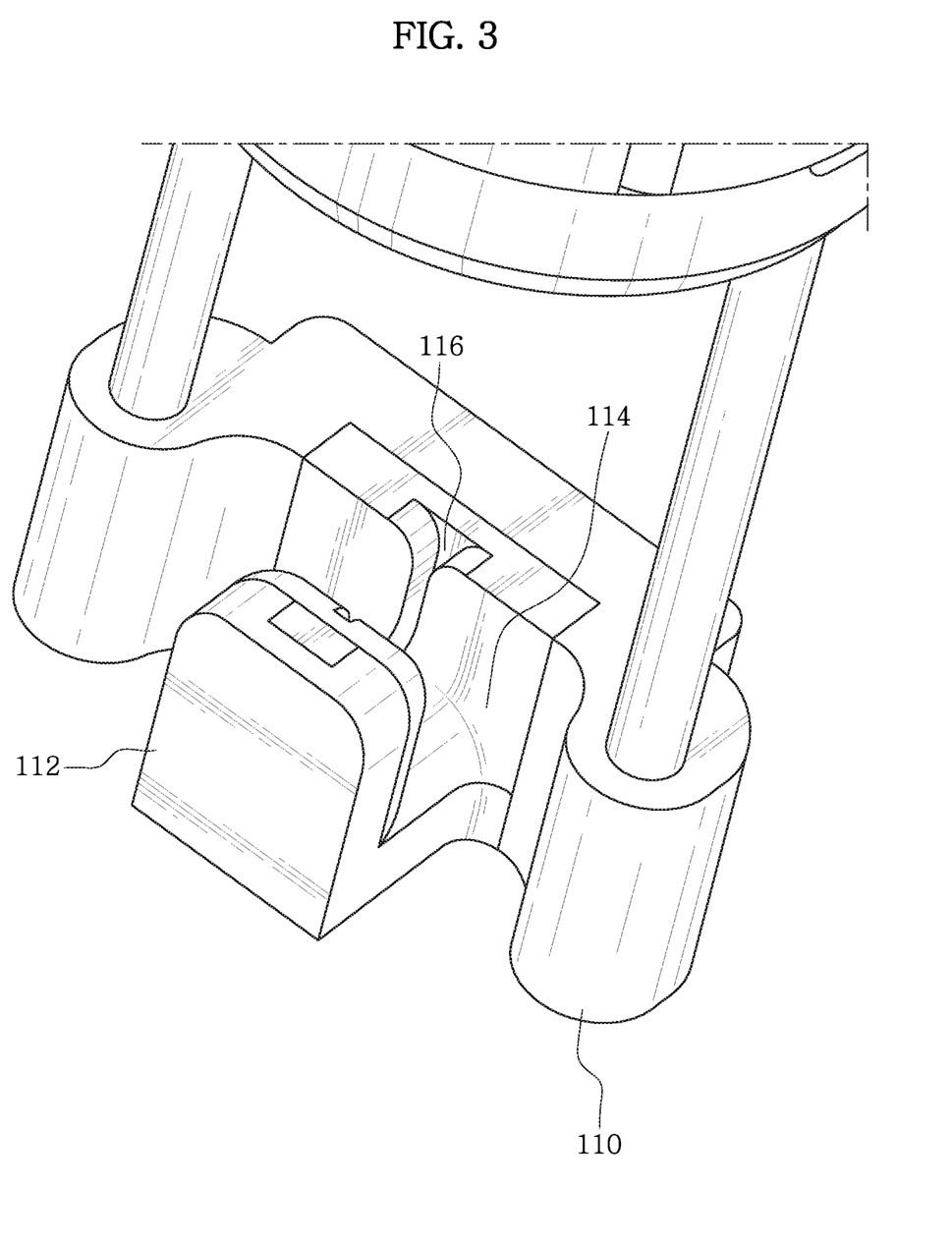
FIG. 3 shows a nerve fixing part of the apparatus for inserting an electrode structure of FIG. 1.

FIG. 3 shows the nerve fixing part 110 of the apparatus 100 for inserting an electrode structure of FIG. 1.

As shown in FIG. 3, the nerve fixing part 110 includes a protrusion 112, a nerve fixing groove 114, and an alignment slit 116.

The protrusion 112 protrudes from the flat plate of the nerve fixing part 110 with a predetermined width and thickness to facilitate the placement of the nerve. The protrusion 112 includes the nerve fixing groove 114 in a upper side. Because the nerve fixing groove 114 is where a direct contact with the nerve is made, at least a portion may be made of a soft material to prevent the nerve from being damaged. For example, the nerve fixing groove 114 may be made of soft elastomer such as polyurethane. As shown in FIG. 3, the nerve fixing groove 114 is defined by a first side wall and a second side wall facing each other across a center surface, the center surface defining a base of the nerve fixing groove 114.

The alignment slit 116 may run through the protrusion 112 or extend to the end of the protrusion 112 along the longitudinal axis of the nerve fixing part 110. The alignment slit 116 provides a space so that the electrode structure 144 can be easily inserted into the flexible nerve. The horizontal width of the alignment slit 116 is almost equal to or larger than the width of the electrode structure 144 so that the electrode structure 144 can move through the alignment slit 116. As the gap of the alignment slit 116 is narrower, the bottom of the flexible nerve may be fixed more securely, and thus the gap of the alignment slit 116 may be almost equal to or a little larger than the thickness of the electrode structure 144. The corners of the alignment slit 116 may be rounded to induce the electrode structure 144 to be inserted more easily and reduce damage of the nerve. When the nerve fixing groove 114 is made of soft elastomer, even though the nerve is stuck in the alignment slit 116 by the pressure at the time of inserting the electrode structure 144, the nerve may easily slip out by the restoring force with reduced damage.

Figure 4:
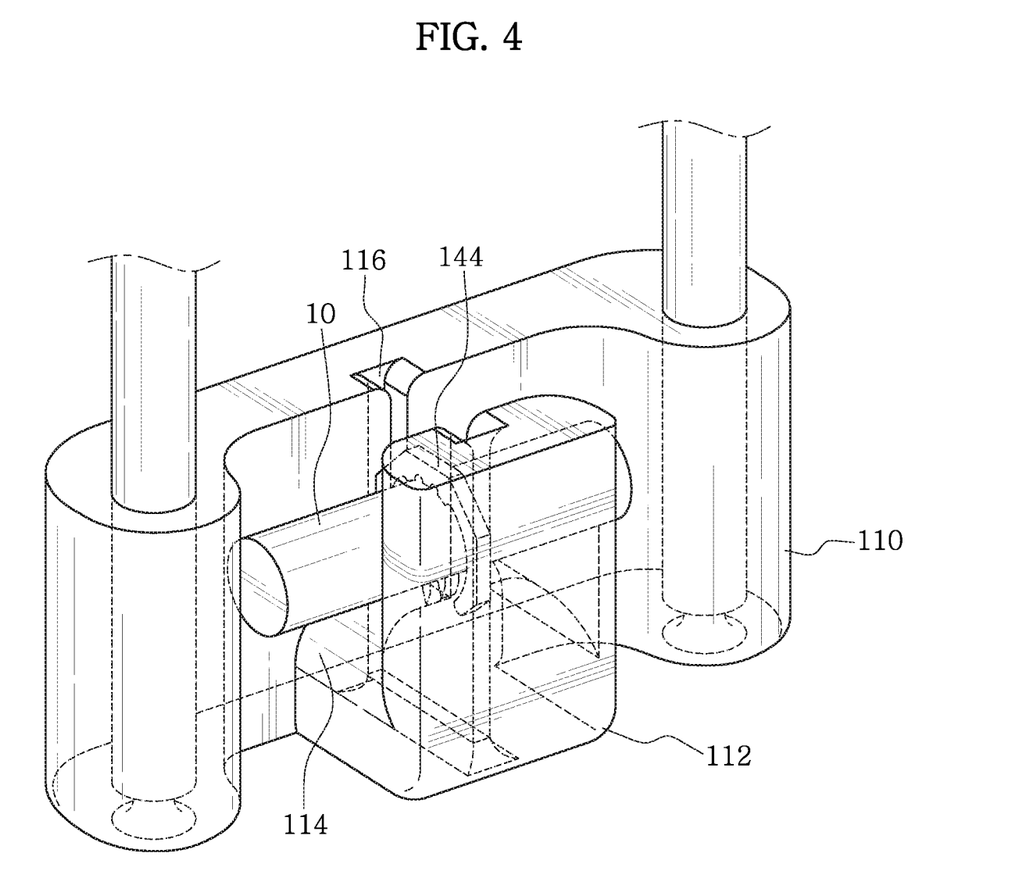
FIG. 4 shows an electrode structure inserted into nerve by the nerve fixing part of FIG. 3.

FIG. 4 shows the electrode structure 144 inserted into the nerve 10 by the nerve fixing part 110 of FIG. 3.

As shown in FIG. 4, the electrode structure 144 moves along the alignment slit 116 and may be stably inserted into the nerve 10 fixed on the nerve fixing groove 114. According to an embodiment of the present disclosure, the nerve fixing groove 114 may have a structure in which the width is adjusted to fit the diameter of the nerve 10. For example, the nerve fixing part 110 may be configured to replace the nerve fixing grooves 114 having different widths. The alignment slit 116 included in the upper side of the nerve fixing groove 114 also may have a structure in which the width and thickness are adjusted or replaced to fit the size of the electrode structure 144. As shown in FIG. 4, the nerve 10 extends in a first direction, and the sliding elements 122 (numbered in FIG. 2) extend in a second direction (insertion direction) crossing the first direction.

Figure 5A:
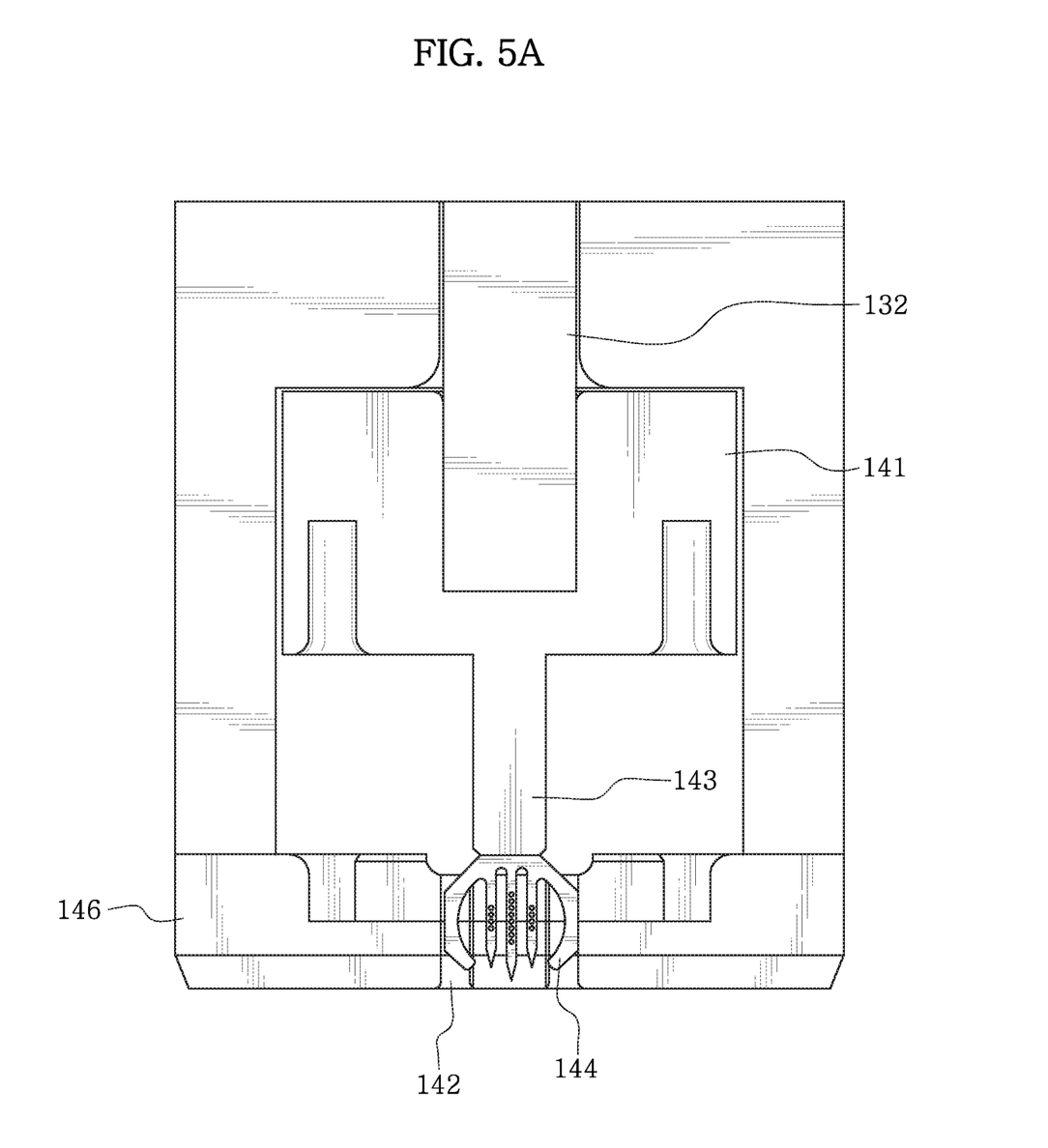
FIGS. 5A and 5B show an electrode structure before and after ejection from an electrode structure ejector of an apparatus for inserting an electrode structure according to an embodiment of the present disclosure.
Figure 5B:
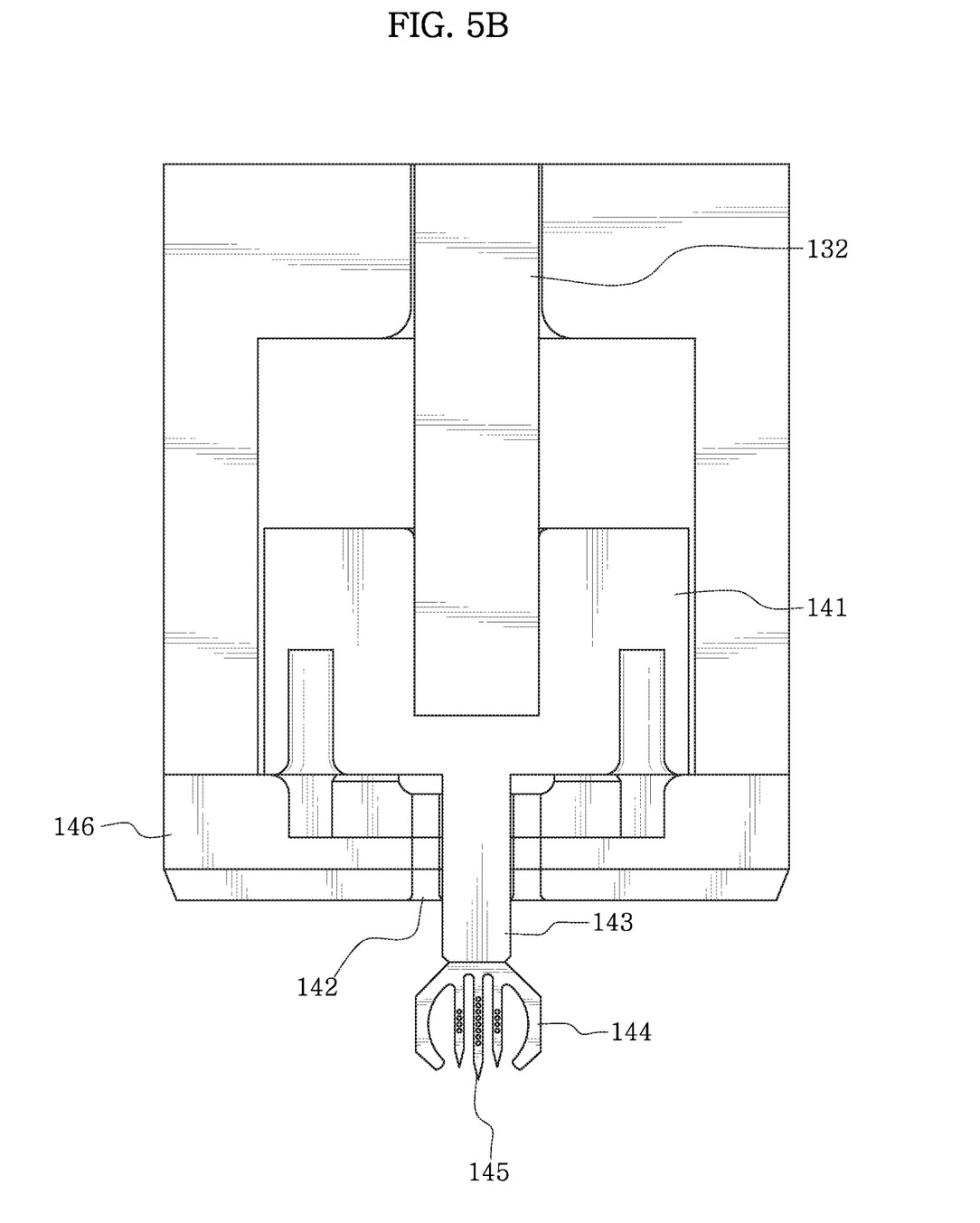

FIGS. 5A and 5B show the electrode structure 144 before and after ejection from the electrode structure ejector 140 of the apparatus 100 for inserting an electrode structure according to an embodiment of the present disclosure.

Referring to FIG. 5A, an ejector body 141 of the electrode structure ejector 140 is connected to a support 143 having a narrower width, and the end of the support 143 comes into contact with the mounted electrode structure 144. As the electrode structure 144 has a width that nearly matches the opening 142, the electrode structure 144 may be fixed in the mounting part that leads from the opening 142. In this instance, the electrode structure 144 is loaded in the electrode structure ejector 140. According to another embodiment of the present disclosure, the electrode structure 144 may be loaded such that the electrode structure 144 is attached to the support 143, and the support 143 may be configured to be easily separated from the electrode structure 144 when the electrode structure 144 is inserted into and fixed to the nerve 10. For example, the support 143 may be made of a material having a weak magnetic property and work as described above.

The ejector body 141 of the electrode structure ejector 140 is connected to the center pole 132 and receives a force applied from the pressing part 130. The loaded state of the electrode structure 144 of FIG. 5A is a state before the electrode structure 144 slips out of the opening 142, in which there is no movement of the center pole 132. In other words, it means that even in the case in which as the nerve fixing part 110 moves, the nerve 10 is disposed in contact with or in proximity to the nerve fixing plate 146, the electrode structure 144 is loaded in the fixed position.

Referring to FIG. 5B, when a force equal to or greater than the critical value is applied from the pressing part 130 connected to the center pole 132, the ejector body 141 connected to the center pole 132, the support 143 and the electrode structure 144 simultaneously move in the direction in which the pressure is applied. In this instance, the second elastic element 162 may be included between the ejector body 141 and the nerve fixing plate 146. In case that the second elastic element 162 is included, only when a force equal to or greater than the second critical value for causing compression of the second elastic element 162 is applied to the pressing part 130, the ejector body 141, the support 143 and the electrode structure 144 can move. According to an embodiment, the widths of the support 143 and the electrode structure 144 may be smaller than or almost equal to the width of the opening 142, and through this, the support 143 and the electrode structure 144 may be ejected through the opening 142. The ejected electrode structure 144 may be inserted into the nerve 10 fixed below the nerve fixing plate 146.

The electrode structure 144 according to an embodiment of the present disclosure may have a shape of roughly the Korean alphabet letter "ㄷ", including at least one probe 145 in the middle and two supports extending to two sides and having an opening on one surface. Additionally, the electrode structure 144 may have a shape of a thin plate with the thickness that is relatively very thin in comparison to the width.

According to an embodiment of the present disclosure, the electrode structure 144 has a shape of roughly the Korean alphabet letter "ㄷ", but is not limited thereto. Provided that the body of the electrode structure 144 bends to surround in contact with or apart from at least part of the circumference of the nerve 10, the electrode structure 144 may have a shape of, for example, a different polygon with an open surface, and may have a curved shape such as the letter of "C."

The body of the electrode structure 144 may have rounded corners, or at least part of the body may be formed of an elastic material to avoid tissue damage in the human body.

According to an embodiment, the probe 145 of the electrode structure 144 may be integrally formed with the same thickness as the thickness of the body.

Figure 6:
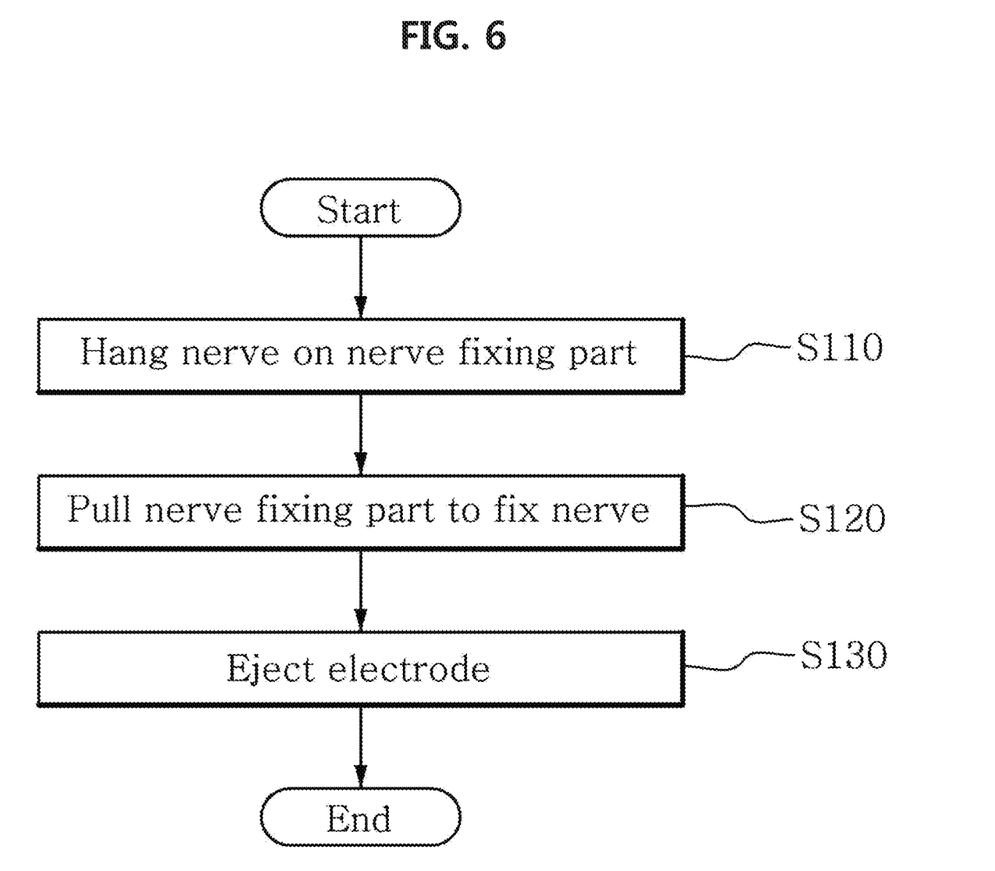
FIG. 6 shows a process of inserting an electrode structure into nerve using an apparatus for inserting an electrode structure according to an embodiment of the present disclosure.

FIG. 6 shows a process of inserting the electrode structure 144 into the nerve 10 using the apparatus 100 for inserting an electrode structure according to an embodiment of the present disclosure.

Referring to FIG. 6, an embodiment of a method for inserting the electrode structure 144 into the nerve 10 using the apparatus 100 for inserting an electrode structure includes hanging the nerve 10 on the protrusion 112 of the nerve fixing part 110 (S110), moving the nerve fixing part 110 to fix the nerve 10 (S120), and ejecting the electrode structure 144 to insert the electrode structure 144 into the nerve 10 (S130).

First, the nerve 10 is hung on the protrusion 112 of the nerve fixing part 110 (S110). In other words, a target site of the nerve 10 into which the electrode structure 144 is to be inserted is hung on and fixed in the protrusion 112 of the nerve fixing part 110. The target site of the nerve 10 into which the electrode structure 144 is to be inserted may be seated in the nerve fixing groove 114 and aligned on the same axis as the electrode structure ejector 140. Through this, the ejected electrode structure 144 may be inserted into a desired location of the nerve 10.

Subsequently, the nerve fixing part 110 is moved to fix the nerve 10 (S120). When the pull lever 120 is pulled, the nerve fixing part 110 connected to the sliding element 122 moves in the pull direction, and the nerve 10 seated in the nerve fixing groove 114 is further fixed when covered with the nerve fixing plate 146. According to an embodiment of the present disclosure, as the depth of the nerve fixing groove 114 is smaller than the diameter of the nerve 10, some areas are disposed outside of the nerve fixing groove 114 and come into contact with the nerve fixing plate 146, thereby effectively fixing the nerve 10. In this instance, the nerve fixing part 110 may be configured to move when a force applied to the pull lever 120 is greater than the first critical value for compressing the first elastic element 161.

Finally, the electrode structure 144 is ejected and inserted into the nerve 10 (S130). According to an embodiment of the present disclosure, when a predetermined force or more is applied to the pressing part 130, the ejector body 141 of the electrode structure ejector 140 moves down through the center pole 132 and the electrode structure 144 is ejected through the opening 142. In this instance, the electrode structure 144 is linearly inserted into the nerve 10 fixed in the nerve fixing groove 114 placed on the same axis as the electrode structure ejector 140. In this instance, the alignment slit 116 is disposed on the same axis as the electrode structure ejector 140, in particular, the electrode structure 144 to assist the linear movement of the electrode structure 144. When the electrode structure 144 is inserted into the nerve 10, the electrode structure 144 moves along the alignment slit 116, and as the gap of the alignment slit 116 is narrower, the bottom of the flexible nerve 10 may be fixed more securely. The gap of the alignment slit 116 may be properly formed in consideration of the thickness of the electrode structure 144. According to another embodiment of the present disclosure, the nerve fixing part 110 may be configured to have the controllable gap of the alignment slit 116, or may be configured to be replaceable with the nerve fixing groove 114 including the alignment slits 116 of different thicknesses.

Figure 7A:
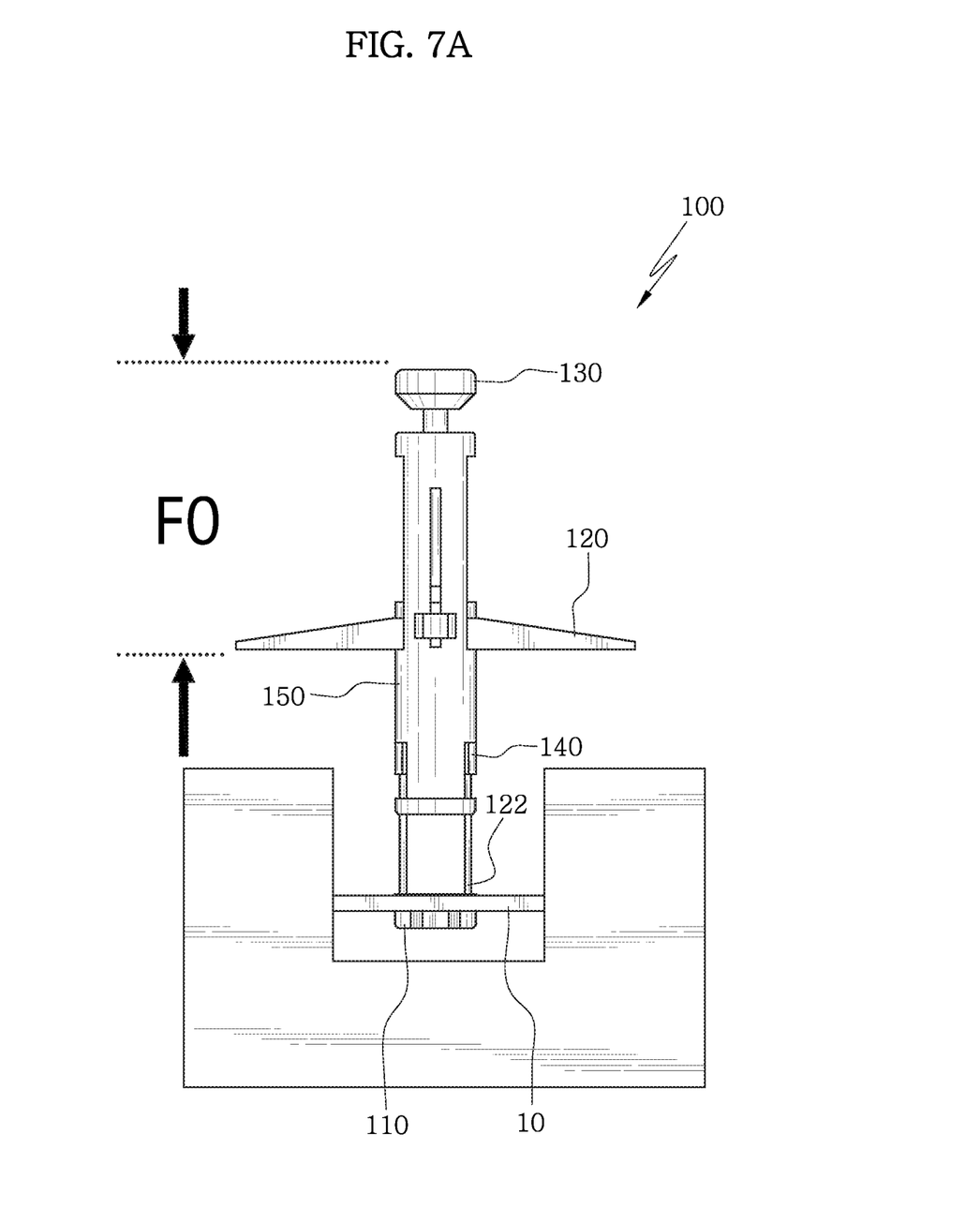
FIG. 7A to 7C show changes in the electrode structure inserted condition in each step in which a force is applied to an apparatus for inserting an electrode structure according to an embodiment of the present disclosure.
Figure 7B:
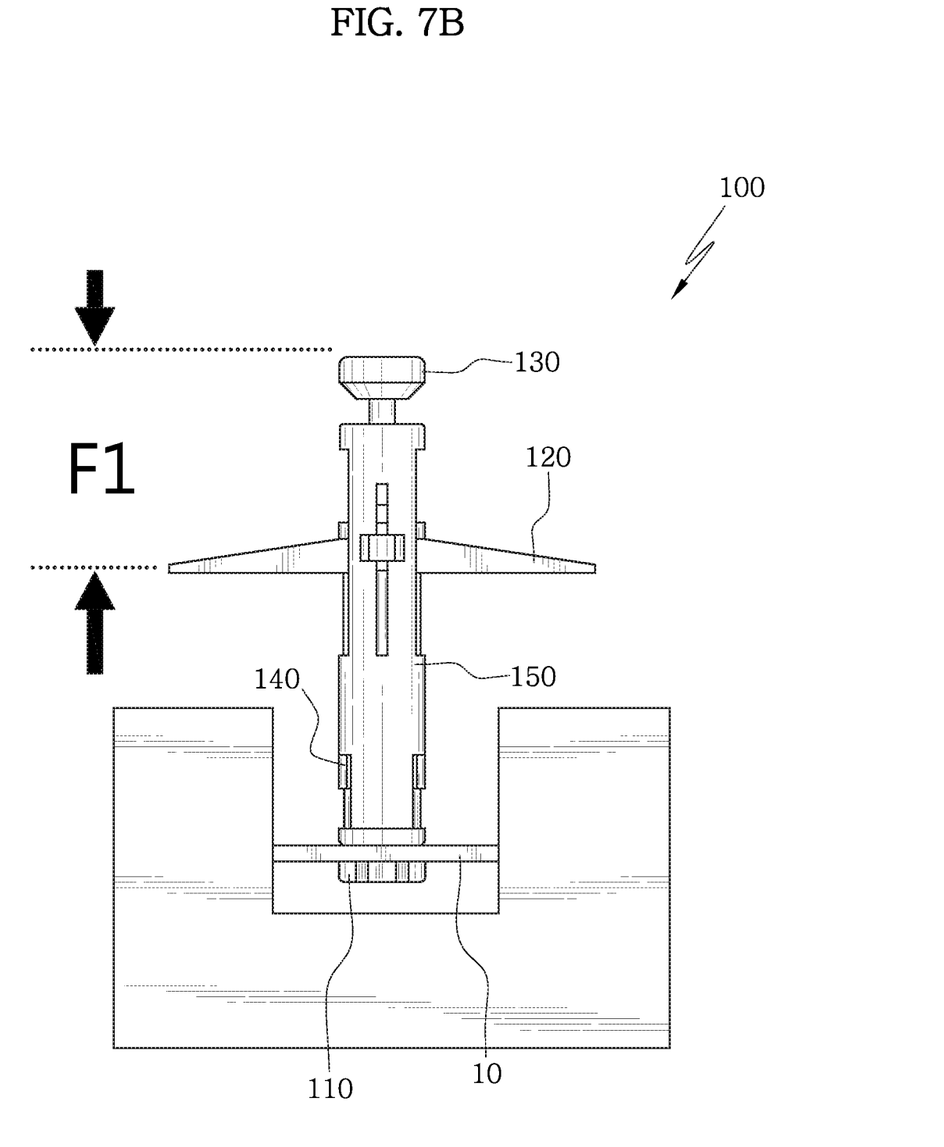
Figure 7C:
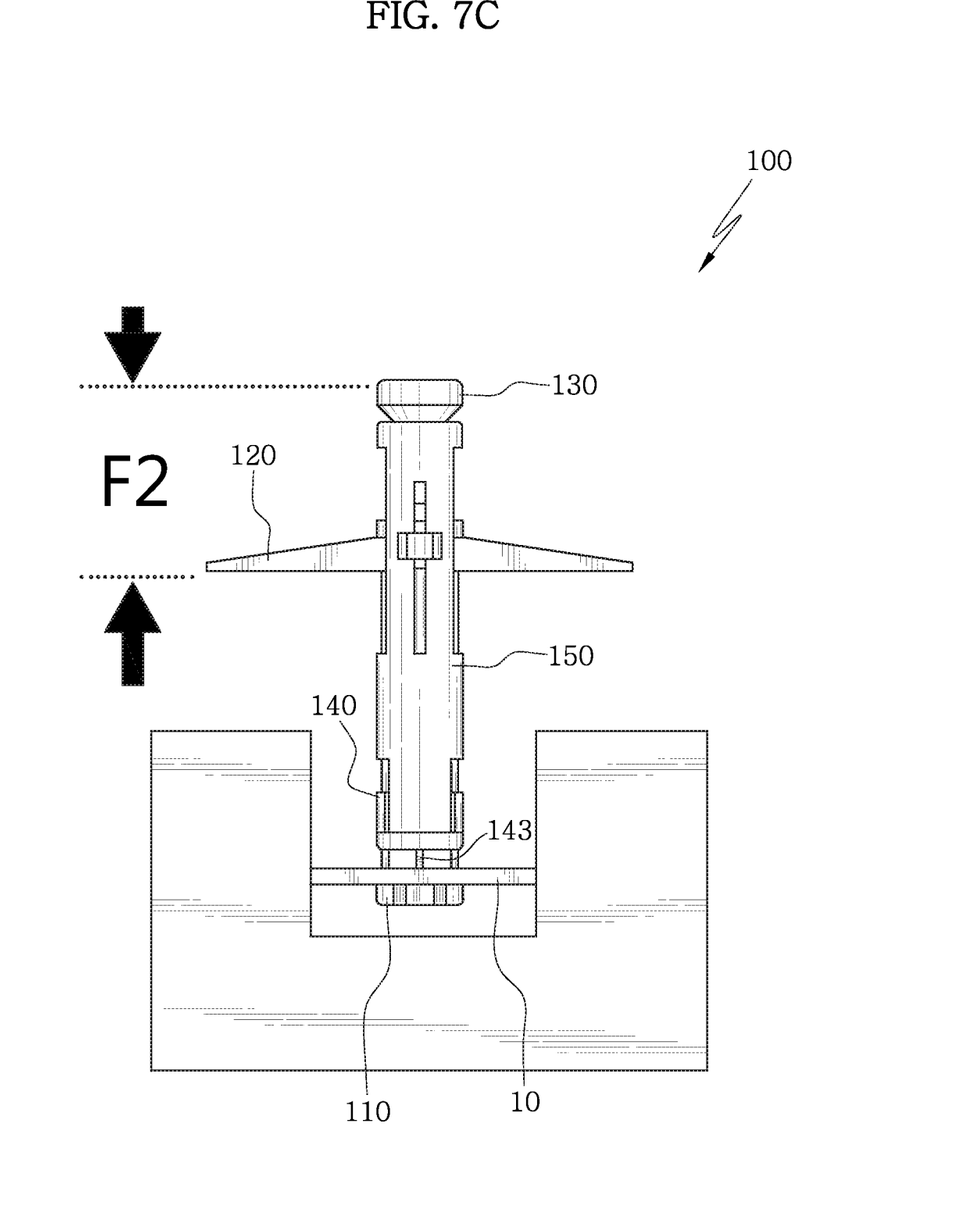

FIG. 7A to 7C show the changes in the inserted condition of the electrode structure 144 in each step in which a force is applied to the apparatus 100 for inserting an electrode structure according to an embodiment of the present disclosure.

According to an embodiment of the present disclosure, the process of inserting the electrode structure 144 into the nerve 10 using the apparatus 100 for inserting an electrode structure of FIG. 6 may be each shown in FIGS. 7A to 7C. Particularly, FIGS. 7A to 7C show the process of inserting the electrode structure 144 sequentially using the apparatus 100 for inserting an electrode structure including the two elastic elements 161, 162 having different stiffness.

Referring to FIG. 7A, first, the nerve fixing part 110 is put near the nerve 10, and the nerve 10 is hung on the nerve fixing part 110 (S110). Although the following description provides that the apparatus 100 for inserting an electrode structure is used with the thumb in contact with the pressing part 130 and the index and middle fingers in contact with two arms of the pull lever 120, respectively, for convenience of description, the present disclosure is not limited thereto. According to another embodiment of the present disclosure, a force applied to the pressing part 130 and the pull lever 120 may be applied through an assistive device by an electrical circuit configuration. In the step of hanging the nerve 10 on the nerve fixing part 110, a force of F0 may be applied between the thumb and the index/middle finger. When the magnitude of F0 is smaller than the first critical value $F_{fix}$, there is no change in the length of the apparatus 100 for inserting an electrode structure. The first critical value $F_{fix}$ refers to the magnitude of an elastic or restoring force when the first elastic element 161 starts to be compressed.

Referring to FIG. 7B, subsequently, the nerve fixing part 110 is moved to fix the nerve 10 (S120). According to an embodiment of the present disclosure, in the step of fixing the nerve 10, a force of F1 may be applied between the thumb and the index/middle finger. When the magnitude of F1 is greater than the first critical value $F_{fix}$ and smaller than the second critical value $F_{etrd}$, the first elastic element 161 is compressed, but the second elastic element 162 is not compressed and there is no change in length. The second critical value $F_{etrd}$ refers to the magnitude of an elastic or restring force at the point in time when the second elastic element 162 starts to be compressed.

Referring to FIG. 7C, finally, the electrode structure 144 is ejected and inserted into the nerve 10 (S130). According to an embodiment of the present disclosure, in the step of ejecting the electrode structure 144, a force of F2 may be applied between the thumb and the index/middle finger. When the magnitude of F2 is greater than the second critical value $F_{etrd}$, the first elastic element 161 as well as the second elastic element 162 are compressed. The electrode structure ejector 140 moves by the F2 force applied to the pressing part 130, the second elastic element 162 is compressed, and the electrode structure 144 is ejected through the opening 142. The ejected electrode structure 144 is inserted into the nerve 10 fixed in the nerve fixing part 110 on the same axis. In this instance, the ejected electrode structure 144 moves linearly along the alignment slit 116 of the nerve fixing part 110 and is inserted into the nerve 10.

Figure 8:
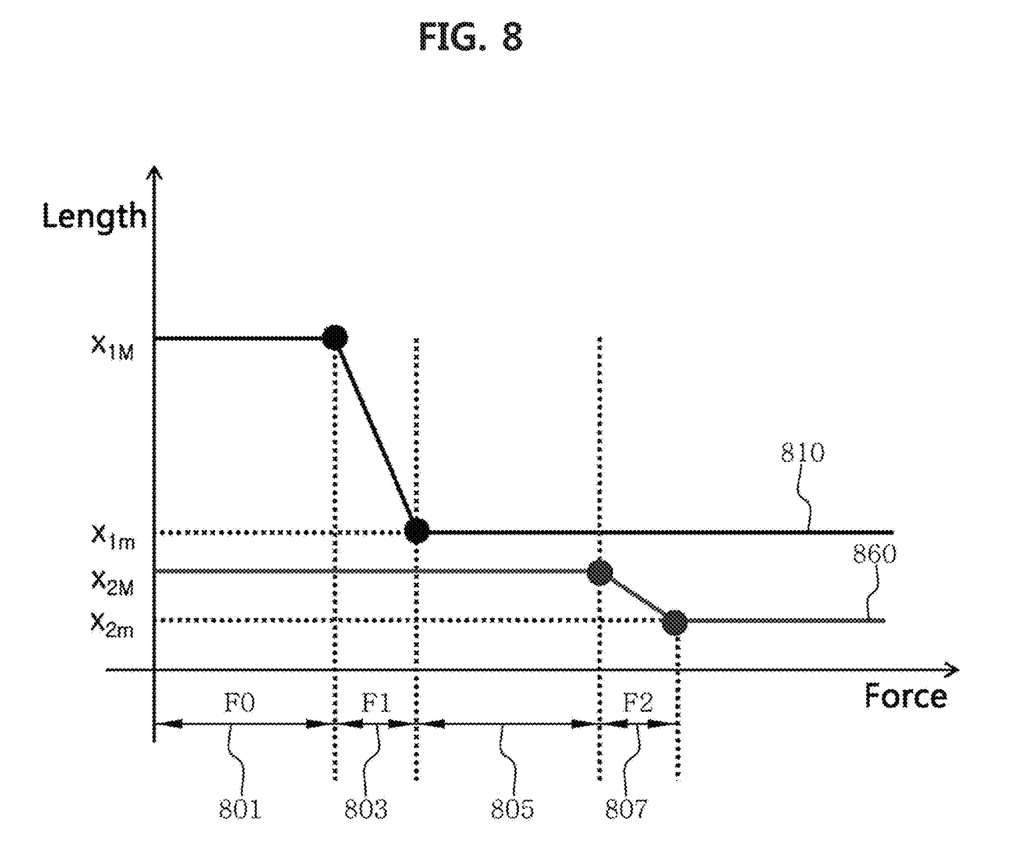
FIG. 8 shows length changes of an elastic element in each step in which a force is applied to an apparatus for inserting an electrode structure according to an embodiment of the present disclosure.

FIG. 8 shows the length changes of the elastic elements 161, 162 in each step in which a force is applied to the apparatus 100 for inserting an electrode structure according to an embodiment of the present disclosure.

Referring to FIG. 8, a graph 810 shows the length changes of the first elastic element 161 and a graph 860 shows the length changes of the second elastic element 162, in response to changes in the magnitude of a force applied to the apparatus 100 for inserting an electrode structure. The force applied to the apparatus 100 for inserting an electrode structure is divided into an F0 range 801, an F1 range 803, a margin range 805, and an F2 range 807 by the magnitude of the force.

The F0 range 801 is a range in which the magnitude of a force applied to the apparatus 100 for inserting an electrode structure is smaller than the first critical value $F_{fix}$ and the second critical value $F_{etrd}$. For example, the F0 range 801 is a range in which a force of the magnitude of F0 in FIG. 7A acts, and there is no change in the length of the apparatus 100 for inserting an electrode structure. In the F0 range 801, the initial length of the first elastic element 161 is $X_{1M}$ and the initial length of the second elastic element 162 is $X_{2M}$ without change in length, and thus the apparatus 100 for inserting an electrode structure also has no change in the length. According to an embodiment of the present disclosure, in the F0 range 801, the magnitude of a force applied to the pressing part 130 and the pull lever 120 of the apparatus 100 for inserting an electrode structure is less than the first critical value $F_{fix}$ even though it increases, and thus the second elastic element 162 as well as the first elastic element 161 are not compressed and there is no change in length.

The F1 range 803 is a range in which the magnitude of a force applied to the apparatus 100 for inserting an electrode structure is equal to or greater than the first critical value $F_{fix}$, and is smaller than the second critical value $F_{etrd}$. For example, the F1 range 803 is a range in which a force of the magnitude of F1 in FIG. 7B acts and the nerve fixing part 110 of the apparatus 100 for inserting an electrode structure moves in the pull direction. According to an embodiment of the present disclosure, in the F1 range 803, when the magnitude of a force applied to the pressing part 130 and the pull lever 120 of the apparatus 100 for inserting an electrode structure is equal to or greater than the first critical value $F_{fix}$, the first elastic element 161 starts to be compressed. As the first elastic element 161 is compressed, the length of the first elastic element 161 is reduced from $X_{1M}$ to $X_{1m}$, and the nerve fixing part 110 moves in the pull direction so that the nerve 10 is fixed between the nerve fixing part 110 and the nerve fixing plate 146. In the F1 range 803, as the first elastic element 161 is compressed and reduces in the length, the restoring force increases, and the magnitude of a force required while the length of the first elastic element 161 is reduced to $X_{1m}$ gradually increases. In this instance, because the magnitude of the force applied is less than the second critical value $F_{etrd}$, the second elastic element 162 is not compressed and there is no change in length.

The margin range 805 is a range in which the first elastic element 161 is compressed up to the critical value and is not compressed any longer, but the magnitude of force is less than the second critical value $F_{etrd}$. In other words, the margin range 805 is a range that is formed due to a difference between the magnitude of force at the compression end point of the first elastic element 161 and the magnitude of force at the compression start point of the second elastic element 162, and varies depending on configurations of the first elastic element 161 and the second elastic element 162. For example, there is almost scarcely a margin range 805, or the margin range 805 may be extremely short, depending on the stiffness of the first elastic element 161 and the second elastic element 162.

The F2 range 807 is a range in which the magnitude of a forced applied to the apparatus 100 for inserting an electrode structure is equal to or greater than the second critical value $F_{etrd}$. For example, the F2 range 807 is a range in which a force of magnitude of F2 in FIG. 7C acts and the electrode structure ejector 140 of the apparatus 100 for inserting an electrode structure ejects the electrode structure 144 to insert the electrode structure 144 into the nerve 10. According to an embodiment of the present disclosure, in the F2 range 807, when the magnitude of a force applied to the pressing part 130 and the pull lever 120 of the apparatus 100 for inserting an electrode structure is equal to or greater than the second critical value $F_{etrd}$, the second elastic element 162 also starts to be compressed. As the second elastic element 162 is compressed, the length of the second elastic element 162 is reduced from $X_{2M}$ to $X_{2m}$, and the electrode structure ejector 140 moves and the electrode structure 144 is ejected through the opening 142. The ejected electrode structure 144 is inserted into the nerve 10 fixed in the nerve fixing part 110. In the F2 range 807, as the second elastic element 162 is compressed and reduces in the length, the restoring force increases, and the magnitude of a force required while the length of the second elastic element 162 is reduced to $X_{2m}$ gradually increases.

In the specific embodiments described above, the elements included in the present disclosure are represented in singular or plural form according to the presented specific embodiments. However, representation in singular or plural form is selected suitably for presented situations for convenience of description, and the above-mentioned embodiments are not limited by single or multiple elements, and even the elements represented in plural form may be singular and even the elements represented in singular form may be plural.

Although the present disclosure has been described with regard to the specific embodiments, many modification may be made thereto without departing from the scope of the technical spirit that inheres in various embodiments. Therefore, the scope of the present disclosure should not be confined to the described embodiments and should be defined by the appended claims and equivalents thereto.

[Detailed Description of Main Elements]

| | |
|---|---|
| 10: Nerve | |
| 100: Apparatus for inserting an electrode structure | |
| 110: Nerve fixing part | 112: Protrusion |
| 114: Nerve fixing groove | 116: Alignment slit |
| 120: Pull lever | 122: Sliding element |
| 130: Pressing part | 132: Center pole |
| 140: Electrode structure ejector | 141: Ejector body |
| 142: Opening | 143: Support |
| 144: Electrode structure | 145: Probe |
| 146: Nerve fixing plate | 150: Body |
| 152: Movement element | 154: Movement groove |
| 161: First elastic element | 162: Second elastic element |

What is claimed is:

1. An apparatus for inserting an electrode structure into a nerve in tissue of a living body, the apparatus for inserting an electrode structure comprising:

a nerve fixing part configured to have at least part of a nerve positioned thereon; and an electrode structure ejector connected to the nerve fixing part by a sliding element, the electrode structure ejector configured to have the electrode structure mounted on the electrode structure ejector, the electrode structure ejector configured to move linearly in an insertion direction along the sliding element towards the nerve to insert the electrode structure into the part of the nerve positioned on the nerve fixing part, wherein the nerve fixing part is configured to have the nerve extending in a first direction across a center portion of the nerve fixing part when the nerve is positioned on the nerve fixing part, the first direction crossing the insertion direction, wherein a first line extending in the insertion direction and passing through a center of the nerve fixing part is separated from the sliding element, wherein the nerve fixing part includes an alignment slit extending parallel to the insertion direction and configured to receive an end of the electrode structure to assist a linear movement of the electrode structure, and wherein the alignment slit is configured to allow the electrode structure to move along the alignment slit to be inserted into the nerve.

2. The apparatus for inserting an electrode structure according to claim 1, further comprising:
a pull lever configured to move the nerve fixing part to further fix the nerve to a front end of the apparatus for inserting an electrode structure.

3. The apparatus for inserting an electrode structure according to claim 2, further comprising:
a pressing part which applies a force to the electrode structure ejector to move the electrode structure in the insertion direction.

4. The apparatus for inserting an electrode structure according to claim 3, further comprising:
a first elastic element disposed on top of the nerve fixing part to fix the nerve fixing part, wherein the first elastic element is compressed when a force equal to or greater than a first critical value is applied; and
a second elastic element disposed on bottom of the electrode structure ejector to fix the electrode structure ejector, wherein the second elastic element is compressed when a force equal to or greater than a second critical value is applied.

5. The apparatus for inserting an electrode structure according to claim 4, wherein the second critical value is greater than the first critical value.

6. The apparatus for inserting an electrode structure according to claim 1, wherein at least part of the nerve fixing part that touches the nerve when the nerve is positioned on the nerve fixing part is made of elastomer.

7. The apparatus for inserting an electrode structure according to claim 1, wherein the nerve fixing part includes a first side wall and a second side wall facing each other across a center surface, the first side wall and the second side wall defining walls of a fixing groove which fixes a position of the nerve, and the center surface defining a base of the fixing groove.

8. The apparatus for inserting an electrode structure according to claim 7, wherein the first side wall includes a first slit extending from a top of the first side wall toward the center surface in the insertion direction, the first slit having a depth less than a thickness of the first side wall, the second side wall includes a second slit extending from a top of the second side wall toward the center surface in the insertion direction, the second slit having a depth less than a thickness of the second side wall, and the first slit and the second slit are spaced apart from each other at a distance corresponding to a width of the electrode structure to allow the electrode structure to move along the first and second slits to be inserted into the nerve.

9. The apparatus for inserting an electrode structure according to claim 1, wherein the electrode structure includes at least one probe which is configured to penetrate the nerve and has an electrode.

10. The apparatus for inserting an electrode structure according to claim 1, wherein the electrode structure ejector includes a mounting part having a size matching a width of the electrode structure, the mounting part configured to have the electrode structure mounted in the mounting part, and wherein the electrode structure ejector is configured such that, as the electrode structure ejector moves in the insertion direction, a force is applied to a rear end of the electrode structure and thereby the electrode structure ejector is configured to eject the electrode structure through an opening connected to the mounting part.

11. The apparatus for inserting an electrode structure according to claim 1, wherein the nerve fixing part has a convex shape in which the center of the nerve fixing part is configured to have the nerve positioned thereon and ends of the nerve fixing part curve away from the center and away from the nerve when the nerve is positioned on the nerve fixing part.

12. The apparatus of claim 1, wherein the sliding element includes at least two sliding elements extending substantially parallel to each other between the nerve fixing part and the electrode structure ejector.

13. The apparatus of claim 12, wherein the at least two sliding elements include two sliding elements connected to opposite ends of the nerve fixing part, such that the center of the nerve fixing part configured to have the nerve positioned thereon is located between the two sliding elements.

14. An apparatus, comprising:
a nerve fixing part configured to have at least part of a nerve positioned thereon;
an electrode structure ejector connected to the nerve fixing part by a sliding element, the electrode structure ejector configured to have an electrode structure mounted on the electrode structure ejector, the electrode structure ejector configured to move linearly in an insertion direction along the sliding element towards the nerve to insert the electrode structure into the part of the nerve positioned on the nerve fixing part;
a pull lever configured to move the nerve fixing part to further fix the nerve to a front end of the apparatus for inserting an electrode structure;
a pressing part which applies a force to the electrode structure ejector to move the electrode structure in the insertion direction;
a first elastic element disposed on top of the nerve fixing part to fix the nerve fixing part, wherein the first elastic element is compressed when a force equal to or greater than a first critical value is applied; and
a second elastic element disposed on bottom of the electrode structure ejector to fix the electrode structure ejector, wherein the second elastic element is compressed when a force equal to or greater than a second critical value is applied.

* * * * *